United States Patent
Heslot et al.

(10) Patent No.: US 11,430,542 B2
(45) Date of Patent: Aug. 30, 2022

(54) COMPUTER IMPLEMENTED METHOD FOR PREDICTING TRUE AGRONOMICAL VALUE OF A PLANT

(71) Applicant: LIMAGRAIN EUROPE, Saint Beauzire (FR)

(72) Inventors: Nicolas Heslot, Riom (FR); Stéphanie Chauvet, Aubière (FR); Chloé Boyard, Saulzet-le-Chaud (FR); Pascal Flament, Aubière (FR)

(73) Assignee: LIMAGRAIN EUROPE, Saint Beauzire (FR)

( * ) Notice: Subject to any disclaimer, the term of this patent is extended or adjusted under 35 U.S.C. 154(b) by 1087 days.

(21) Appl. No.: 15/746,907

(22) PCT Filed: Jul. 23, 2015

(86) PCT No.: PCT/IB2015/001372
§ 371 (c)(1),
(2) Date: Jan. 23, 2018

(87) PCT Pub. No.: WO2017/013462
PCT Pub. Date: Jan. 26, 2017

(65) Prior Publication Data
US 2019/0228839 A1  Jul. 25, 2019

(51) Int. Cl.
| | | |
|---|---|---|
| G16B 20/20 | (2019.01) | |
| C12Q 1/6895 | (2018.01) | |
| C12Q 1/68 | (2018.01) | |
| G16B 20/00 | (2019.01) | |
| G16B 5/20 | (2019.01) | |
| G16B 50/20 | (2019.01) | |
| G16B 40/30 | (2019.01) | |
| G16B 40/00 | (2019.01) | |
| G16B 20/40 | (2019.01) | |
| G06N 7/00 | (2006.01) | |

(52) U.S. Cl.
CPC .............. *G16B 20/20* (2019.02); *C12Q 1/68* (2013.01); *C12Q 1/6895* (2013.01); *G06N 7/005* (2013.01); *G16B 5/20* (2019.02); *G16B 20/00* (2019.02); *G16B 20/40* (2019.02); *G16B 40/00* (2019.02); *G16B 40/30* (2019.02); *G16B 50/20* (2019.02); *C12Q 2600/13* (2013.01)

(58) Field of Classification Search
None
See application file for complete search history.

(56) References Cited

FOREIGN PATENT DOCUMENTS

WO    2012/075125 A1    6/2012

OTHER PUBLICATIONS

Piepho H P et al., "Blup for phenotypic selection in plant breeding and variety testing", Euphytica, Kluwer Academic Publishers, vol. 161, No. 1-2, p. 209-228, 2007.
Clark, Samuel A. et al., "Genomic best linear unbiased prediction (gBLUP) for the estimation of genomic breeding values", Methods in Molecular Biology, Humana Press, Inc, vol. 1019, p. 321-330, 2013.
Zhang, Zhe et. al., "Best Linear Unbiased Prediction of Genomic Breeding Values Using a Trait-Specific Marker-Derived Relationship Matrix", PLOS ONE, vol. 5, No. 9, 2010.
Albrecht, T. et. al., "Genome-based prediction of maize hybrid performance across genetic groups, testers, locations, and years.", Theor. Appl. Genet., 2014.
Bernardo, R., "Molecular markers and selection for complex traits in plants: Learning from the last 20 years" Crop Sci. vol. 48, p. 1649-1664, 2008.
De Los Campos, G. et. al., "Reproducing kernel Hilbert spaces regression: a general framework for genetic evaluation", J. Anim. Sci., p. 1883-1887, 2009.
Endelman, J. B. et. al., "Shrinkage estimation of the realized relationship matrix", Genes, Genomes, and Genetics, vol. 2, p. 1405-1413, 2012.
Endelman, J. B. et. al., "Optimal design of preliminary yield trials with genome-wide markers", Crop Sci., vol. 54, p. 48-59, 2014.
Fernando, R. L. et. al., "Optimal properties of the conditional mean as a selection criterion", Theor. Appl. Genet., vol. 72, p. 822-825, 1986.
Habier, D. et. al., "The impact of genetic relationship information on genome-assisted breeding values", Genetics, vol. 177, p. 2389-2397, 2007.
Henderson, C. R., "Applications of linear models in animal breeding" University of Guelph, 1984.
Jia, Y. et. al., "Multiple-trait genomic selection methods increase genetic value prediction accuracy", Genetics, vol. 192, p. 1513-1522, 2012.
Lande, R. et. al., "Efficiency of marker-assisted selection in the improvement of quantitative traits" Genetics, vol. 124, p. 743-756, 1990.
Moreau, L. et. al., "Experimental evaluation of several cycles of marker-assisted selection in maize", Euphytica, vol. 137, p. 111-118, 2004.
Servin, B. et. al., Toward a theory of marker-assisted gene pyramiding. Genetics, vol. 168, p. 513-523, 2004.

(Continued)

*Primary Examiner* — G Steven Vanni
(74) *Attorney, Agent, or Firm* — Oliff PLC (57) ABSTRACT

A computer implemented method for predicting an agronomical value and a breeding value of a plant belonging to a population, the method includes the steps of: obtaining at least some genotypic data from a subset of lines from the population, obtaining at least some phenotypic data from a subset of lines from the population, providing a statistical model receiving in input the genotypic data and phenotypic data, using the statistical model to output at least an agronomical value estimated for the plant. More particularly, the statistical model is a mixed model combining fixed effects and random effects.

15 Claims, 6 Drawing Sheets

(56) References Cited

OTHER PUBLICATIONS

Smith, A. B. et al., "The analysis of crop cultivar breeding and evaluation trials: an overview of current mixed model approaches" J. Agric. Sci., vol. 143, p. 449-462, 2005.
Stuber, C. W. et. al., "Improvement of yield and ear number resulting from selection at allozyme Loci in a maize population" Crop Sci., vol. 22, p. 737-740, 1982.
Tanksley, S. D. et. al., "RFLP Mapping in Plant Breeding: New Tools for an Old Science" Bio/Technology, vol. 7, p. 257-264, 1989.
Vitezica, Z. G. et. al., "On the Additive and Dominant Variance and Covariance of Individuals Within the Genomic Selection Scope" Genetics, vol. 195 p. 1223-1230, 2013.
T. H. E. Meuwissen et. al., "Prediction of Total Genetic Value Using Genome-Wide Dense Marker Maps", Research Institute of Animal Science and Health, Genetics, vol. 157, p. 1819-1829, 2001.
P. M. VanRaden, "Efficient Methods to Compute Genomic Predictions", J. Dairy Sci., vol. 91, p. 4414-4423, 2008.
May 4, 2016 International Search Report issued in International Patent Application No. PCT/IB2015/001372.
Technow, F. et al. "Genomic Prediction of Hybrid Performance in Maize with Models Incorporating Dominance and Population Specific Marker Effects", Theor Appl Genet, No. 125, pp. 1181-1194, Jun. 26, 2012.
Su, G. et al. "Estimating Additive and Non-Additive Genetic Variances and Predicting Genetic Merits Using Genome-Wide Dense Single Nucleotide Polymorphism Markers" PLOS one, vol. 7, No. 9, Sep. 2012.
Mar. 26, 2021 Observation by Third Party Against European Patent Application issued in European Patent Application No. 15784751.8.

COMPUTER IMPLEMENTED METHOD FOR PREDICTING TRUE AGRONOMICAL VALUE OF A PLANT

The present invention relates to a computer implemented method to identify plants such as field crops (maize, barley, wheat, sunflower, rapeseed, etc.) or vegetable crops (tomato, etc.), with desired features.

Usually, breeders estimate the agronomical value of a plant for different traits (height, flowering time, yield, etc.) on the basis of phenotype data collected on that plant.

However, external parameters such as weather and soil conditions, agricultural practices, pests and diseases, etc., have a random effect on phenotype data. From this randomness results a high statistical variability of the estimation of the different traits thus leading to an impaired estimation of the agronomical value of the plant (line or hybrid, as a general tested variety). In practice, numerous experiments are usually needed (locations, years of successive trials, etc.) to accurately estimate the agronomical value of that line or of that hybrid. Therefore, in order to get a reliable statistic value, many locations of trials and many years of successive trials are needed with associated cost.

Moreover, in the presence of genetic non-additive effects, the line best for their agronomical value estimated only on phenotypic data might not be the best parents. Thus selecting the parents of the new lines based only on their phenotypic data may be inefficient.

The present invention aims to improve that situation.

According to a feature of the invention, genotypic data of a plant are used, in addition to phenotypic data, so as to better estimate at least the true agronomical value of that plant.

To that end, a computer implemented method according to the invention uses a statistical model. This model is a mixed model which combines fixed effects (such as those related to a tester effect, or effect of major genes, or season of seed production), and random effects (such as the effect of alleles substitutions at markers loci), with, for example, epistasis, dominance, additive effects). This mixed model receives then, as inputs, genotypic data of a plant (line or hybrid), and, when available, phenotypic data of that plant, and then outputs the prediction of at least the aforesaid true agronomical value of that plant (which can be termed hereafter GEAV, for the "Genomic Estimate of Agronomical Value").

Therefore, the invention aims a computer implemented method for predicting an agronomical value and a breeding value of a plant belonging to a population, the method comprising the steps of:
- obtaining at least some genotypic data from a subset of lines from the population;
- obtaining at least some phenotypic data from a subset of lines from the population;
- providing a statistical model receiving in input said genotypic data and phenotypic data;
- using said statistical model to output at least an agronomical value estimated for said plant;

wherein said statistical model is a mixed model combining fixed effects and random effects.

According to the invention, "plant population" is a set of plants analyzed together by the computer implemented method.

The two subsets from the population according to the invention can be totally, partially or not redundant.

Phenotypic data as genotypic data from the subset of plants can be collected on these plants directly but also on their ascendants, parents or genetically related plant, etc.

According to an advantage of the invention, the present invention enables the use of such an agronomical value prediction to increase the probability of selecting superior plants for their total genetic value, over a selection based on phenotype alone.

In an embodiment, the mixed model is used to output further a breeding value estimated for said plant.

According to an advantage of that embodiment, the use of such a breeding value prediction increases the probability of selecting superior plants as parents of subsequent progeny (breeding value), over a selection based on phenotype alone.

In an embodiment, said genotypic data comprise genetic markers data (such as molecular markers).

In an embodiment, said mixed model further receives in input phenotypic data of said plant.

In this embodiment, said phenotypic data can comprise field trial information data. In fact, said phenotypic data can result from plants phenotyping (typically comprising testing of breeding progeny in traits, such as plant height and plant architecture, male and female flowering date, yield, lodging, biotic and abiotic susceptibility, robustness, etc.). Such phenotypic data can thus include for example at least one trait among crop yield, male and female flowering date, height, biotic and abiotic stress tolerance, ear placement score, plant shape, etc., resulting from observations on plots. In one embodiment, the field trials are performed with several plots (or replicates). The aforesaid traits can be measured from yield trial or from nursery plots. Lab experiment can also be done for some traits (baking quality, digestibility, metabolites quantifications). Phenotypic data can also be more complex traits such the tolerance to drought estimated by the scope of regression of yield of stress index or such as trait calculated using indirect assay (NIRS, image analysis, etc.). In an alternative embodiment, when such traits are not available, genotypic data can be used alone to estimate the true agronomical value. For example, before first trials, an exclusively genotypic model can be used as for said "mixed model" (based on molecular markers only, typically). Then, results obtained after first trials (phenotypic data) can then be updated in the mixed model so as to refine prediction, for example.

In an embodiment, said model comprises a Genomic Best Linear Unbiased Prediction (GBLUP).

In an embodiment, a Gaussian Kernel can be used to estimate a covariance between individuals and capture non-additive genetic effects. In an embodiment also, other marker-based kinship data can be used to estimate covariance of at least one additional non-additive genetic effect (e.g. capturing dominance or pairwise epistasis).

In an embodiment where the method is applied to hybrid crops performance prediction (with male and female effect), the method can further include a step of estimating a dominance effect and/or a non-additive effect based on genotypic data (molecular markers) to capture heterosis.

In an embodiment corresponding to a further refinement of the model where, instead of using one trait at a time, several traits are analyzed simultaneously (making it possible to further increase precision of prediction), said mixed model analyses simultaneously several phenotype traits with a covariance estimated between traits (e.g. earliness and yield) or a same trait being observed in several different environments (e.g. yield in Western Europe and yield in Eastern Europe for maize).

In an embodiment, said mixed model uses at least one additional fixed effect covariate to model an effect of alleles substitutions at markers loci (or QTL) on phenotypic data of said plant (such as for example the effect of a dominant gene which provides almost complete resistance to a virus).

In an embodiment, the method includes tests of said mixed model with heterogeneous residuals.

Preferably, the tests are performed to automatically select the best mixed model. To that end, in a possible embodiment, the method can comprise a step of fitting one error variance per environment (e.g. plot or crop or plot plus crop), instead of a global variance error. Preferably, among converging models, the best model is then selected according to said preferred criterion. Use of heterogeneous residuals modelling can be needed to accommodate data with large variations in quality between trials. Preferably, a best mixed model is selected based on said tests, according to a preferred criterion (such as for example the Akaike's Information Criterion—AIC).

In an embodiment, the method comprises a preliminary step of filtering said phenotypic and/or genotypic data so as to remove at least samples having incomplete data (or low quality data). This can be done using an automatic detection and removal of outlier observations and/or individuals.

In an embodiment, said mixed model more particularly outputs data related to so-called "Genomic Estimate of Genetic Value" (or "GEGV" hereafter) and "Genomic Estimate of Breeding Value" ("GEBV"). The aforesaid agronomical value of a plant (called also hereafter GEAV, for "Genomic Estimate of Agronomical Value") corresponds to its GEGV, while the aforesaid estimated breeding value corresponds to the GEBV. In an embodiment, these GEGV and GEBV values are given with prediction quality estimates.

Further developments can provide:
a tester effect for testcross data,
the use of automatic quality control of molecular markers (on percentage of missing data per individual and marker, on congruence with pedigree data, on expected heterozygosity rate, etc.),
automatic fitting of a factor as fixed or random depending on the number of levels of that factor,
automatic return of analysis without markers if the dataset is too small to be reliably analyzed with markers.

Other developments can include:
combination of several numerical methods to obtain a convergence of the variance estimation when the base numerical method does not converge,
the optional inclusion of pedigree data when available,
finally, backsolving of the model solution to derive marker effects for the "additive" part. Those marker effects can be further used to predict the variance of a putative cross' progenies using simulations or analytical formulas and then to select the pairs of parents with the highest potential: i.e. with the highest probability of generating progenies with superior predicted agronomical or breeding value The present invention aims also at a computer program comprising instructions to perform the method here above, when such instructions are executed by a processor. Such computer program can use multi-threading to speed up computation or use graphical processing units (GPU).

The present invention aims also at a device comprising at least a processor (among other computer means such as a working memory, a non-volatile storage memory, GPU units, communication interfaces, peripheral interfaces, etc.) for executing the method of the invention (typically when reading instructions of said computer program).

The present invention is illustrated by way of example, and not by way of limitation, in the figures of the accompanying drawings, in which like reference numerals refer to similar elements and in which.

Until now, genomic predictions were focused on the breeding value (value in a cross) for unobserved plants. However, according to one aspect of the invention, the total genetic value (i.e. agronomical or commercial value, both being synonymous in the present context) is of interest in a product development context.

Typically, characters of a plant, such as crop yield, flowering date, biotic and abiotic tolerance, height, etc., are related to its agronomical value. A plant might have superior agronomical value in the field of farmers but may have a poor breeding value and hence generate low quality progenies and conversely.

The inclusion of markers enables to smooth the year and environment effect as if the candidate line, in early yield trial, was tested over more plots (more replicates and more environments). In the presence of epistasis though, the inclusion of marker data in the model can be counterproductive to the accuracy of the agronomical value estimation if the wrong statistical model is used (e.g. if non-additive effects are present and not adequately modelled). Therefore several statistical models are tested in turn on the particular data set including one that does not use marker info at all to make sure that the retained agronomical value estimates (the retained fitted model) are at least as accurate as those provided by the traditional basic model that uses phenotypic data only.

Figure 1:
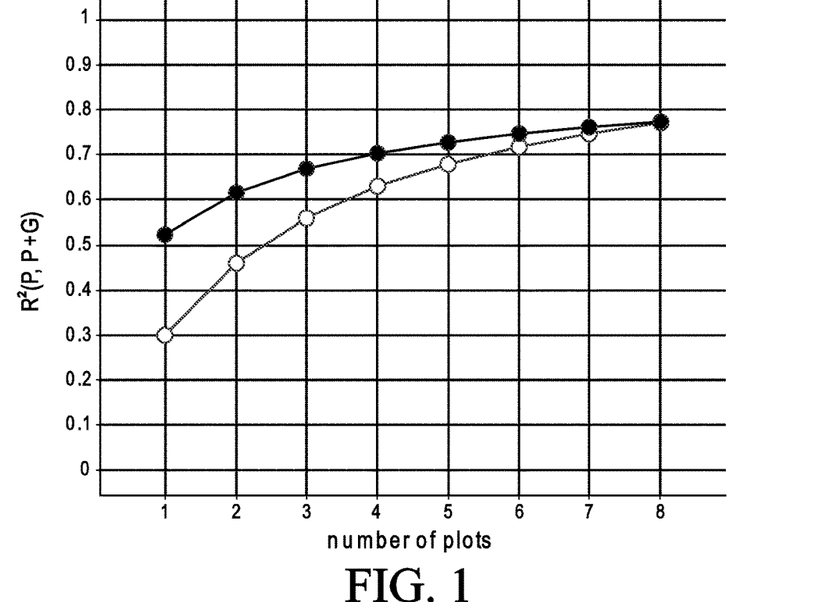
FIG. 1 shows a difference between predictions simply based on phenotype P (white dots) and based on a combination of phenotypic and genetic data P+G (black dots)

FIG. 1 shows some of those results:
1) white disks are related to the expected precision (simulation) of the phenotype "P" depending on the numbers of plots observed for a plant,
2) black disks are related to the expected precision when markers add to phenotype "P+G" are used to analyze the trial on a same number of plots for the same plant (based on simulation results with the following hypothesis: repeatability 0.3 and epistasis variance=20% of total genetic variance) so as to predict a commercial value of that plant.

To efficiently implement the systematic use of markers, methods are needed to make sure that the analysis model is always at least as good as a model without markers to predict the total genetic value of the plant.

A separate prediction of the breeding value is needed to select the best parents, in a model always including markers to separate additive from non-additive effects.

A number of other issues to solve are linked to data quality control, optimal use of the available data and automatic data cleaning.

Beyond the breeding value/total genetic value prediction task, there are many alternatives to improve the model. An efficient model selection procedure is needed however for automation.

The present invention makes it possible to analyze field trials systematically with molecular markers not only data generated on the last year but all relevant data generated in the past by breeding activities and use them for selection decision.

A description of a mixed model that can be used to that end is given now, in light of embodiments that have been presented in the prior art mainly in the field of animal breeding, an overview of which is presented hereafter.

The use of molecular markers is disclosed for example in:
STUBER C. W., GOODMAN M. M., MOLL R. H., 1982 *Improvement of yield and ear number resulting from selection at allozyme Loci in a maize population.* Crop Sci. 22: 1-4.
TANKSLEY S. D., YOUNG N. D., PATERSON A. H., BONIERBALE M. W., 1989 *RFLP Mapping in Plant Breeding: New Tools for an Old Science.* Bio/Technology 7: 257-264.
LANDE R., THOMPSON R., 1990 *Efficiency of marker-assisted selection in the improvement of quantitative traits.* Genetics 124: 743-756.
MOREAU L., CHARCOSSET A., GALLAIS A., 2004 *Experimental evaluation of several cycles of marker-assisted selection in maize.* Euphytica 137: 111-118.
BERNARDO R., 2008 *Molecular markers and selection for complex traits in plants: Learning from the last 20 years.* Crop Sci. 48: 1649-1664.

Use of molecular markers as an aid to selection has been an active area of research for several decades now (STUBER et al. 1982; TANKSLEY et al. 1989; LANDE and THOMPSON 1990) and has generated a lot of expectations, but early results have been quite disappointing for complex quantitative traits (MOREAU et al. 2004; BERNARDO 2008) such as yield in crops.

As another way of identifying plants with desired characteristics, genomic selection ("GS" hereafter) fostered great hopes and opened new ways to use molecular markers in breeding for complex traits:
MEUWISSEN T., HAYES B. J., GODDARD M., 2001 *Prediction of total genetic value using genome-wide dense marker maps.* Genetics 157: 1819-29.

Initially, most of the research was conducted in the animal breeding community, where the high cost of phenotyping (e.g., here progeny testing in dairy cattle breeding), as well as the impossibility to replicate individuals, made it attractive. In addition, partly because of the impossibility to replicate individuals, animal breeders implemented mixed model methodology early on to analyze their data using the available pedigree information:
HENDERSON C. R., 1984 *Applications of linear models in animal breeding.* University of Guelph, Guelph, Ontario.

In plant breeding, the use of mixed models is more recent:
SMITH A. B., CULLIS B. R., THOMPSON R., 2005 *The analysis of crop cultivar breeding and evaluation trials: an overview of current mixed model approaches.* J. Agric. Sci. 143: 449-462.
PIEPHO H. P., MOHRING J., MELCHINGER A. E., BUCHSE A., 2007 *BLUP for phenotypic selection in plant breeding and variety testing.* Euphytica 161: 209-228.

Marker-assisted recurrent selection (hereafter "MARS") refers to several breeding schemes using markers to select unphenotyped individuals and then crossing them to generate the next generation from selected candidates. Initial work with MARS used biparental or multi parental population and QTL detection (QTL for "Quantitative Trait Loci") and then tried to pyramid QTL:
SERVIN B., MARTIN O. C., MÉZARD M., HOSPITAL F., 2004 *Toward a theory of marker-assisted gene pyramiding.* Genetics 168: 513-23.

Only markers significantly associated with the trait were used in the recurrent selection process. As a consequence, some genomic selection (GS) reports make a distinction between MARS and GS but it is rather more logical to consider GS as a tool to carry out MARS and other uses.

The genomic selection (GS) or prediction is defined here as the simultaneous use of genome-wide markers to predict an individual's total genetic or breeding value for both observed and unobserved individuals. Multi-trait GS models can make use of information on correlated traits to improve prediction accuracy, as presented in:
JIA Y., JANNINK J.-L., 2012 *Multiple-trait genomic selection methods increase genetic value prediction accuracy.* Genetics 192: 1513-22.

Early work on GS in plants was mainly focused on unobserved individuals, in the MARS context. GS can be beneficial for observed individuals as well if entry-mean heritability is low:
ENDELMAN J. B., ATLIN G. N., BEYENE Y., SEMAGN K., ZHANG X., SORRELLS M. E., JANNINK J.-L., 2014 *Optimal design of preliminary yield trials with genome-wide markers.* Crop Sci. 54: 48-59.

GS can be performed with a variety of statistical methods. Those methods are concerned with the same so-called "large P small n" problem: there are many more predictor P (marker) effects to be estimated than there are observations n. Most approaches to this problem involve some type of penalized regression. Currently, the most widely used model is the genomic best linear unbiased prediction model (GBLUP):
HABIER D., FERNANDO R. L., DEKKERS J. C. M., 2007 *The impact of genetic relationship information on genome-assisted breeding values.* Genetics 177: 2389-97.

With GBLUP, markers are used to estimate the covariance between individuals. That information is further used in a mixed model analysis to predict performance of observed and unobserved individuals. The GBLUP model has the advantage of relative simplicity, limited computing time and well-known optimality properties of mixed models for selection:
FERNANDO R. L., GIANOLA D., 1986 *Optimal properties of the conditional mean as a selection criterion.* Theor. Appl. Genet. 72: 822-5.

A classic GBLUP mixed model for genetic evaluation can be written:

$$y = X\beta + Zu + \varepsilon \quad (1)$$

y is a vector of phenotype,
X is a design matrix,
β is a vector of non-genetic effects such as environments with design matrix X.
u is a vector of genetic effects with design matrix Z and ε is a vector of residuals.

If all m individuals are replicated in all t locations and β is a vector of location (or, more generally, environment) effects (weather, soil, etc.), then:

$$\beta = I_t \otimes l_m \text{ and}$$

$$u = l_t \otimes I_m$$

$I_t$ is an identity matrix with t rows and $l_m$ is a vector of ones with length m.
⊗ is the Kronecker product.
The error variance is usually:

$$\text{var}(\varepsilon) = I\sigma_\varepsilon^2$$

The simplest form of this model does not use pedigree or markers and assumes that individuals are unrelated such that:

$$\text{var}(u) = I\sigma_g^2$$

$\sigma_g^2$ is the genetic variance.

The estimate of u would then be a simple adjusted phenotypic mean. This estimate can be further refined by assuming that individuals are related such that their performances are not independent from each other.

Then, the variance is such that:

$$\text{var}(u) = K\sigma_a^2 \text{ and}$$

$\sigma_a^2$ is an additive genetic variance, K being kinship which can be based on pedigree (often called then relationship matrix) or on markers (then often called the "realized relationship matrix"). If W is the centered markers score matrix (representing thus a "genetic similarity" matrix) with m rows and as many columns as markers (W' being the transposed matrix of W), then one way of calculating K is $$K = \frac{WW'}{2\sum_k p_k(1 - p_k)}$$

$p_k$ is the frequency of the minor allele:
VANRADEN P. M., 2008 Efficient methods to compute genomic predictions. J. Dairy Sci. 91: 4414-23.

There are some other possibilities for kinship K to capture some non-additive effects:
LOS CAMPOS G. DE, GIANOLA D., ROSA G. J. M., 2009 Reproducing kernel Hilbert spaces regression: a general framework for genetic evaluation. J. Anim. Sci. 87: 1883-7.

If some individuals are not phenotyped, they still can be predicted by the model. In that case, some columns of Z contain only zero elements. Predictions are obtained by solving the mixed model equations once the variances are estimated:

$$\begin{pmatrix} \hat{\beta} \\ \hat{u} \end{pmatrix} = C \begin{pmatrix} X'y \\ Z'y \end{pmatrix} \text{ with}$$

$$C = \begin{pmatrix} X'X & X'Z \\ Z'X & Z'Z + K^{-1}\frac{\sigma_\varepsilon^2}{\sigma_a^2} \end{pmatrix}^{-}$$

where the exponent "−" designates the generalized inverse matrix.

This model can be further extended to predict hybrid performance by adding an additional random effect such that:

$$y = X\beta + Z_1 u_1 + Z_2 u_2 + \varepsilon \quad (2)$$

y, β and ε are as before, while $u_1$ and $u_2$ are, respectively, male and female genetic effect (which can be observed in plants such as maize, sunflower or rapeseed for example), such that $$\text{var}(u_1) = K_1 \sigma_{a1}^2 \text{ and } \text{var}(u_2) = K_2 \sigma_{a2}^2 \text{ with:}$$

$\sigma_{a1}^2$ and $\sigma_{a2}^2$ additive genetic variance in the male and female groups, respectively, and,
$K_1$ and $K_2$ relationship matrices based on pedigree or markers for each group:

ALBRECHT T., AUINGER H.-J., WIMMER V., OGUTU J. O., KNAAK C., OUZUNOVA M., PIEPHO H. P., SCHÖN C.-C., 2014 Genome-based prediction of maize hybrid performance across genetic groups, testers, locations, and years. Theor. Appl. Genet.

When Model (1) is calibrated on non-inbred material and Model (2) can accommodate an additional random effect $u_3$ to capture dominance effects, such that:

$$\text{var}(u_3) = K_3 \sigma_d^2 \text{ with } \sigma_d^2 \text{ dominance variance, and}$$

$$K_3 = \frac{VV'}{2\sum_k p_k^2(1 - p_k)^2}$$

V is a centered marker design matrix for the dominance effect such that each column of that matrix V corresponds to a marker with minor allele a of frequency p coded:

$$\{aa, Aa, AA\} = \{-2p^2, 2p(1-p), -2(1-p)^2\}$$

as explained in:
VITEZICA Z. G., VARONA L., LEGARRA A., 2013 On the Additive and Dominant Variance and Covariance of Individuals Within the Genomic Selection Scope. Genetics: 1-26.

While $K_1$ and $K_2$ correspond to kinship between males and females for example, $K_3$ has one row per hybrid.

Model (2) (with or without markers) can be described as a GCA model (general combining ability)

From the overview given above, it appears that genomic selection has been mainly described as a way to shorten selection by selecting on the basis of markers only. It was recently realized (ENDELMAN et al. 2014) that the use of markers could also improve the precision of selection based on phenotypic data, even at constant cost:

ENDELMAN J. B., JANNINK J.-L., 2012 Shrinkage estimation of the realized relationship matrix. Genes, Genomes, and Genomics 2: 1405-1413.

The method of the invention brings a conceptual change with the introduction of separate analysis for total agronomical value ("genetic value" as usually named in the prior art) and breeding value (value as a parent). This distinction was not possible without markers and is believed as novel, at least in the field of plant breeding. In fact, in the agronomical field, a seed of a fixed genotype has in itself an agronomical value, for the future plant growing directly from that seed is identical to the mother plant. In the field of animal breeding, the breeding value (for crossing) is usually the sole and important value to take into account so as to assign a value (e.g. a commercial value) to a genitor (bull, dam, etc.).

It is however a major improvement over current practices, in the field of agronomy. Plant breeders can then select individuals based on agronomical value prediction to advance toward release, and furthermore pick potentially different individuals as parents of new individuals based on breeding value prediction.

There are some potential issues with the introduction of molecular markers. However, the invention provides a very flexible and robust pipeline able to automatically deal with potentially low quality data and return reliable prediction, always at least as good as the baseline analysis that does not use markers, as shown below with reference to FIG. 5 for example. Better estimated true agronomical values of selection candidates using GEGV instead of simple phenotypic BLUP (EGV) increase probability of advancing superior genotypes towards release.

Statistical developments in embodiments of the invention include systematic detection of outliers, automatic choice of the most adapted statistical model, better exploitation of low quality trial data and systematic use of historical data generated by breeding programs.

Taken separately, each of those developments is not efficient. A combination of them in a pipeline is needed to maximize breeding efficiency as well as their use in a context of systematic analysis of field trials with molecular markers.

The aforesaid pipeline, using both phenotypic and genetic data, is presented below when referring to FIG. 4 below.

Figure 2:
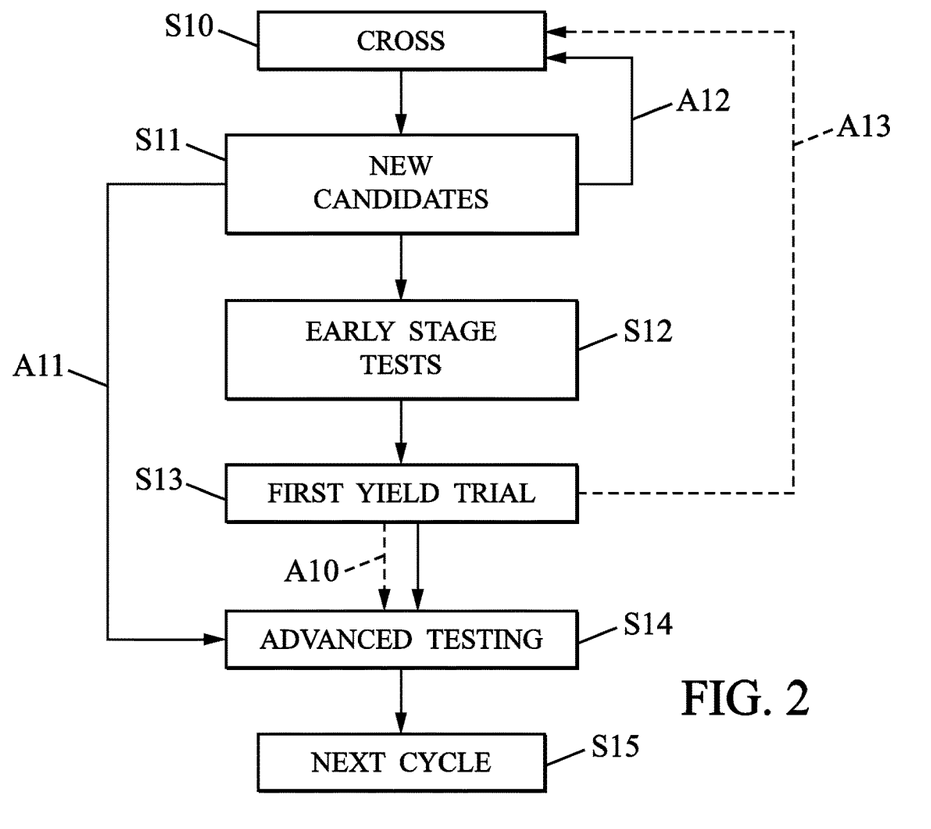
FIG. 2 shows a possible context of application of the method of the invention.

Before presenting such figures in details, an example of context where the invention can be advantageously used is given hereafter with reference to FIG. 2.

In this context given by way of an example, a cross between plant parents is performed at step S10 and generates new candidates (represented as step S11 on FIG. 2): e.g. individual plants, which may include doubled haploids. The new candidates of step S11 can be obtained by repeated selfing of the cross generated in step S10 or by single seed descent or by the mean of double haploids.

First phenotypic data can be obtained at step S12, such as, for example for maize: ear insertion height, plant height, flowering time, disease resistance, etc.

A rapid cycling based on a genomic selection after step S11 can be performed (based essentially in practice on molecular markers only, and not on phenotype parameters) as represented with arrow A12. At an early stage after obtaining new candidates (at step S11) and before obtaining a first yield trial (at step S13) early stage tests can be also performed at step S12 using marker assisted selection for majors QTLs (Quantitative Trait Loci) such as for example major QTLs for disease resistance.

Usually, next step S13 corresponding to a first yield trial is performed and data which are really observed on crop plots are gathered (including agronomical data such as for example plant earliness, resistance to disease, actual yield, weight per kernel, etc.). Traits starting to be collected at this stage are the most important agronomical ones. They are usually the lower heritability traits (lower than those of step S12), with few replicates and few locations (up to a dozen of plots, usually). However, these data can be used for implementing a model (a mixed model) using molecular markers which can estimate better the true agronomical value and the true breeding value of the individuals than the phenotype alone (arrows A13 and A10 in dot lines representing a major contribution of the invention), on the basis of:

Genetic data obtained from step S11, typically including molecular markers combined to Phenotypic data (from step S12 and being completed at step S13) to estimate an estimate of the true agronomic value and breeding value that the mixed model can output.

The model output can be used to select potentially different individuals for enhanced agronomical value (arrow A10) and optionally enhanced value as a parent (breeding value) (arrow A13).

Furthermore, the model results (arrows A10 and A13) can be used to:

give predictions including non-additive effects (such as epistasis for example) to improve true agronomical value prediction predict additive and non-additive genetic values, so as to enhance predictions of individuals resulting from a breeding of the parent plants crossed at step S10, and further individuals resulting from further crossings at next cycle step S15.

The advanced tests performed at step S14, can use phenotypic data collected at step S14 and genetic data (that can be generated at any stage and potentially collected on ascendants or descendants of the plant tested in step S14) for plants advanced directly from step S11 (arrow A11). For plants advanced from step S13 (arrow A10) the tests can use phenotypic data collected in steps S12 and S13.

Here, estimates of the agronomical value for low heritability traits determined in step S13 can be improved, with numerous replicates observed in numerous locations.

A further benefit of the invention is that selection decision using phenotype alone are usually based on only one year of data whereas the invention provides means through the use of molecular markers to use multiple years and data and smooth the impact of the year of trialing of the candidates.

Figure 3:
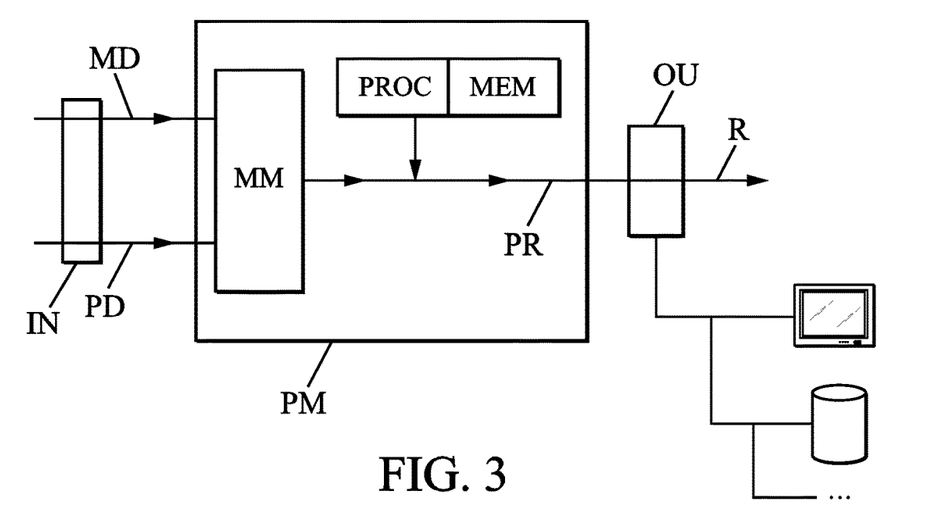
FIG. 3 shows a device for implementing the method of the invention, in a possible embodiment.

With reference now to FIG. 3, a computer device for implementing the method of the invention comprises:

An input interface IN for receiving (among others) genetic data MD (such as molecular markers data), and phenotypic data PD resulting from crop in plots results, Processing means PM comprising at least a processor PROC and a memory unit MEM for implementing a mixed model MM, which delivers, through An output interface OU, a prediction PR giving one or several true genetic values which can be ranked over respective several candidates for a crossing. Such a prediction PR can be used locally (analyzed on a screen for example) or can be transmitted to a distant computer unit (for storage for example in a remote database).

Of course, the content of FIG. 3 is very schematic. For example, the processor PROC can be replaced by multiple processors or a combination of processors and graphical processing units (GPUs) to speed up computation.

An exemplary embodiment of a computer implemented process (the aforesaid "pipeline") is now described with reference to FIG. 4. First steps S41 to S43 of FIG. 4 are related to data retrieval and preparation. These steps can be automatically implemented, advantageously. Step S41 includes for example a marker selection, phenotype data selection, and database queries to that end. Step S42 is related to data filtering (remove non-genotyped entries except checks, remove individuals not initially present in selected trials: this step can be performed in advance during the marker pre-selection for example, and/or its result can be inputted in step S41 so as to update marker data). Step S43 is related to data quality control (with a phenotype quality control so as to give for example minimum and maximum quantitative values for each trait). Data point quality measures collected by experimenters can be used to remove low quality datapoints, for example, data corresponding to plots with a low standcount in maize or with heavy bird damage in cereals. Trials with very few individuals can also be removed automatically based on a threshold.

A marker pre-processing can be performed also so as to take into account for example a call rate (percentage of missing data), pedigree errors (inconsistencies between information related to parent plants and the marker), heterozygosity, etc. in order to improve the quality of the marker data used in the remaining of the analysis and avoid spurious results.

A second group of steps S44 to S46 are related to procedures to determine a convenient choice of analysis options. At step S44, analysis options are chosen involving selections among for example (and not limited to these items):
  an environment type (such as "year×location", or "year× location×trial" in case of field heterogeneities),
  additional fixed effects per trait, e.g. major genes or QTLs (for example, a gene can provide a better and total resistance to a virus, influencing thus phenotype features data),
  use of commercial control checks in the analysis,
  crops types (specific options such as for maize, or rapeseed, etc.) so as to add relevant information (model with testers for maize for example, hybrid model for rapeseed, etc.).

Those selections of information are intended to give relevant information so as to build the model parameters of the vector β (environment effect—year effect—commercial control checks, tester effect), of non-genetic effects in equation (2) given again hereafter and of genetic effects u1 and u2 (u2 is optional):

$$y = X\beta + Z_1 u_1 + Z_2 u_2 + \varepsilon$$

Plant gender information (N1 males and N2 females for example) can be used to define u1 and u2 in a case where hybrid data is analyzed.

As a further option (dashed lines in step S45), a non-additive model can be included in the model selection procedure, for example with additional random effects (more complex model to fit).

Figure 4:
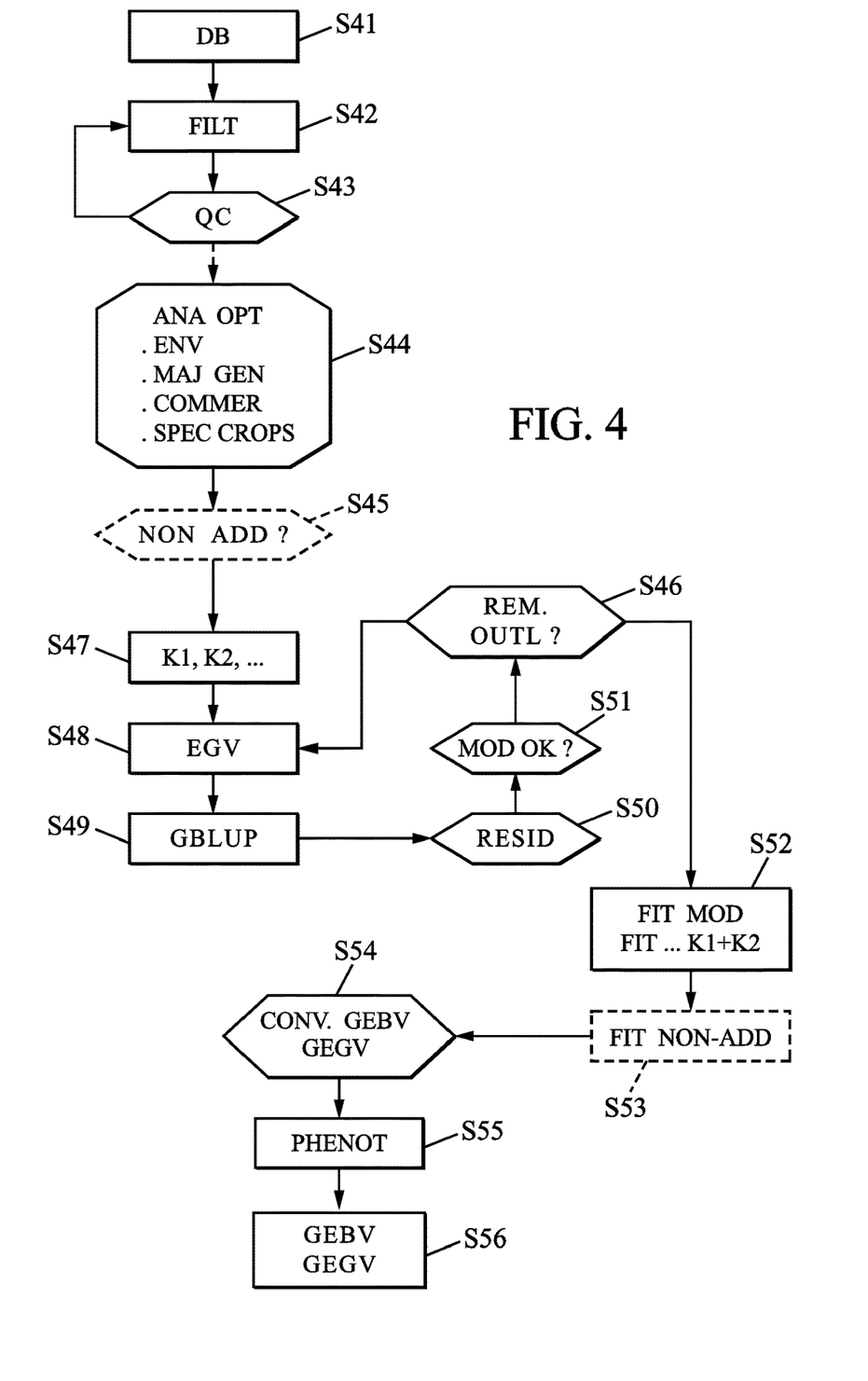
FIG. 4 shows a complete algorithm corresponding to an embodiment of the computer program of the invention.

The next group of steps of FIG. 4 is related to the model selection. An automatic selection of the best model is advantageously provided.

In step S47, kernels (kinship: matrix K1 and K2, Gaussian) and their inverse are computed. In step S48, a rough Estimation of the Genetic Value (EGV) based on phenotype alone is calculated so as to perform basic phenotype analysis. Then, in step S49 a "one-step" GBLUP (Genomic Best Linear Unbiased Prediction) model calculation is performed (as a first rough estimation of the genetic and breeding value with markers, same model at this stage). In step S50, a one-step GBLUP model is calculated now with heterogeneous residuals, so as to test an error variance e for example per environment (in case of a particular crop having suffered from storm or hail, or crop having been eaten by wild boars, etc.) or per any other parameter having a non-genetic effect. Less weight is then given in the model to such bad quality results. In step S51, the model is tested according to a chosen criterion such as the Akaike's Information Criterion (AIC). Then, if heterogeneous residuals are improving the model based on a selection criterion such as the AIC, the corresponding option should be kept for future steps. Once this part of the model is selected, it can be chosen to remove outliers according to a selected threshold (step S46). If outliers are removed, the reduced dataset is an input to step S48 to refit the different models.

Preferably, variance components can be used from a previous model to generate better starting values for the next model to fit (so as to get a faster convergence of the new model). If a model does not converge, the algorithm stops and does not fit more complex models.

In step S52, once the model is validated and outliers potentially removed, a more complex model is fitted, with one (or two in the case of hybrids, like in equation (2) above) additive effect being based on marker and another effect capturing independent epistatic deviation with covariance proportional to identity.

If this model converges, another model is fitted with one additive effect being based on markers and one non-additive effect based on the Hadamard product of the kinship based on markers to capture pairwise epistatic effects.

Optionally, more complex non-additive models using for example the Gaussian kernel can be fitted in step S53 (decision taken in step S45) or models capturing dominance effects. Here again, variance components can be used from previous models to generate better starting values for the new model (so as to get a faster convergence). In step S54, the best models are selected according to the AIC criterion and convergence. Separate selection procedures are used to identify the best model to pick the best parents (using the GEBV: Genomic Estimate Breeding Value) and to identify the best model to predict the agronomical value (also called the GEGV: Genomic Estimated Genetic Value). This "Genetic Value" is the total genetic value. It entails all the genetic components: additive, epistasis and dominance whenever relevant. The workflow can be stopped if a given model does not converge. In step S54, the best model identified for the agronomical value can simply be the EGV (the model for rough Estimation of the Genetic Value, without markers).

Step S55 relates to a prediction rescaling to correspond to phenotype scale.

Preferably, multi-threading can be used to speed up matrix operations, using for example supernodal sparse factorization and inversion in all model fit steps.

Finally, the process outputs in step S56 the GEBV and the agronomical value (GEGV) (predictions with respect to parents and with respect to commercial expectations), as well as:
  Quality results of the prediction estimates (including details of the analysis, graphs, diagnostics),
  Standard errors,
  Graphs of residuals.

Further details of the models which can be used are given below.

For the EGV calculation, a BLUP without markers is used (Best Linear Unbiased Prediction).

For the GEBV calculation, a basic GBLUP (Genomic Best Linear Unbiased Prediction) using Van Raden kinship is performed.

For the Genomic Estimation of Agronomical Value calculation, different approaches are tested. The results from the best one only are output among the following ones:
  "simple EGV";
  same as GEBV (K) (additive effects only);
  "Classic" ($K+K^2$);
  "Independent" (K+diagonal matrix as explained below);
  "Gaussian" (optional; 10 different covariance matrices are tried successively to retain the best fitting one or a quadratic approximation is used. Calculation times are equivalent to 10 fits of basic GBLUP);

k-kernel (optional; 90 different covariance matrices are tried successively to retain the best fitting one. Calculation times are equivalent to 90 fits of basic GBLUP). Therefore, several models can be used to capture non-additive effects and use different covariance structures. Model selection is preferably based on AIC. For more details about the models, the following expressions can be used:

EGV: $y = X\beta + Z_1 u_I + \varepsilon$

GBLUP: $y = X\beta + Z_1 u_K + \varepsilon$

GBLUP-GBLUP2 (classic): $y = X\beta + Z_1 u_K + Z_2 u_{K^2} + \varepsilon$

GBLUP-IDE (independent): $y = X\beta + Z_1 u_K + Z_2 u_I + \varepsilon$

GBLUP-gaussian: $1 \leq i \leq 10, y = X\beta + Z_1 u_{Kg(i)} + \varepsilon$

GBLUP-kkernel: $1 \leq j \leq 90, y = X\beta + Z_1 u_{Kk(j)} + \varepsilon$ where:
y is a known vector of observations
β is an unknown vector of fixed effects
$u_M$ is an unknown vector of random effects with $u_M \sim N(0, M \sigma^2_M)$
ε is an unknown vector of random errors
X and $Z_1$ are known design matrices relating the observations to β and $u_M$, respectively.

For fully epistatic effects ($u_M$ with M=I), an n×n identity matrix I can be provided.

For additive effects only, a VanRaden kinship matrix can be used (as described above):

$$K(n \times n) = \begin{bmatrix} a_{11} & a_{12} & a_{13} & \ldots & a_{1n} \\ a_{12} & a_{22} & a_{23} & \ldots & a_{2n} \\ a_{13} & a_{23} & a_{33} & \ldots & a_{3n} \\ \vdots & \vdots & \vdots & \ddots & \vdots \\ a_{1n} & a_{2n} & a_{3n} & \ldots & a_{nn} \end{bmatrix}.$$

For the GBLUP-Gaussian and for GBLUP-kkernel models, one factor accounts for the sum of additive and non-additive effects. The variance-covariance structure for that factor involves a n×n positive definite (non-diagonal) matrix chosen amongst 10 or 90, respectively, as said above indexed by kernel parameters to be estimated:

$$\begin{bmatrix} a_{11} & a_{12} & a_{13} & \ldots & a_{1n} \\ a_{12} & \begin{bmatrix} a_{11} & a_{12} & a_{13} & \ldots & a_{1n} \\ a_{12} & \begin{bmatrix} a_{11} & a_{12} & a_{13} & \ldots & a_{1n} \\ a_{13} & a_{12} & \begin{bmatrix} a_{11} & a_{22} & a_{13} & \ldots & a_{1n} \\ a_{13} & a_{12} & a_{22} & a_{23} & \ldots & a_{2n} \\ a_{1n} & \vdots & a_{13} & a_{23} & a_{33} & \ldots & a_{3n} \\ & a_{1n} & \vdots & \vdots & \vdots & \ddots & \vdots \\ & & a_{1n} & a_{2n} & a_{3n} & \ldots & a_{nn} \end{bmatrix} \end{bmatrix} \end{bmatrix} \end{bmatrix}.$$

For the Gaussian kernel, the covariance structure is such that the i,j element of that covariance is given by exp $(-(D_{i,j}/\theta)^2)$ where the matrix of Euclidean distances between individuals D is calculated with markers and normalized to the interval [0,1] and θ is a so-called bandwidth parameter estimated by REML using a grid search or quadratic approximation.

For GBLUP-k-kernel model, it is indexed by two parameters k and h such that it is equal to $hS_k + (1-h)S$. h is a mixture parameter that varies between 0 (GBLUP model) and 1 (block-diagonal covariance reduced to the target $S_k$). $S_k$ is a block diagonal matrix with individuals ordered into k clusters, if individuals i and j belong to the same cluster, the corresponding element of $S_k$ is equal to the element of K and 0 otherwise. For a given k, the population is split in k clusters that are determined by transforming K in a distance matrix and using a classical clustering algorithm. That is for a given k, the assignment of individuals to each k clusters is done by a clustering algorithm. The values of k and h are estimated by REML using a grid search. It can be seen as a multiple-kernel model or a simplified multi-trait model.

For the GBLUP-GBLUP2 (classic) model, the $u_{K^2}$ term involves a variance-covariance matrix which is the Hadamard product of the VanRaden matrix by itself.

Theses matrices are multiplied by their respective variance component to provide the factor's variance-covariance structure.

Environment can be modeled as fixed or random effect. If environment is random, an additional random term $Z_{env}u_{env}$ can be part of the model. As an example of workflow, environment can be treated as fixed if it has less than six levels. The term P always contains the intercept and can contain additional fixed effects provided by the user. Tester and commercial checks can be automatically fitted as fixed effects if needed.

The models to choose from are reported in the following table:

| Epistastic Model | Method | Number of genetic effect |
|---|---|---|
| egv | EGV | 1 |
| No | GBLUP | 1 |
| Classic | GBLUP-GBLUP2 | 2 |
| independent | GBLUP-IDE | 2 |
| gaussian | GBLUP-gaussian | 1 |
| kkernel | GBLUP-kkernel | 1 |

If the phenotype is collected on hybrid data, analysis can be done using the parent information, the number of genetic effects is multiplied by two compared to the above description plus other optional effects capturing specific combining ability.

For the EGV, GEBV and GEAV (Genomic Estimate of the Agronomical Value, corresponding to the GEGV), the same models are calculated and compared for each parent independently.

Molecular profiles of parents are used. Several models with different covariance structures are fitted. Model selection is based on AIC.

For the EGV model, a BLUP without markers (parent1 and parent2 being independent) can be used.

For a GEBV model, additive part is to be taken into account. Different models are tested, and only the best one for each component is retrieved. Results can be a mix of several approaches, among:
  basic GBLUP (one kinship for each group of parents: parent1 and parent2)
  Independent for parent2 (K(parent1)+diagonal matrix (parent2))
  Independent for parent1 (diagonal matrix (parent1)+K (parent2))

The following equations can be used:

For EGV: $y=X\beta+G_1u_{I1}+G_2u_{I2}+G_3u_{I3}+\varepsilon$

For GBLUP: $y=X\beta+G_1u_{K1}+G_2u_{K2}+\varepsilon$

For GBLUP-*IDE*: $y=X\beta+G_1u_{K1}+G_2u_{I2}+\varepsilon$ or $y=X\beta+G_1u_{I1}+G_2u_{K2}+\varepsilon$ For GBLUP-*SCA*: $y=X\beta+G_1u_{K1}+G_2u_{K2}+G_3u_{K3}+\varepsilon$ where:
y is a known vector of observations
β is an unknown vector of fixed effects
$u_{Mi}$ is an unknown vector of random effects with $u_{Mi} \sim N(0, M\sigma^2_{Mi})$
ε is an unknown vector of random errors
X and $G_i$ are known design matrices relating the observations to β and $u_{Mi}$, respectively.

A specific combining effect (SCA) based on markers capturing epistasis between parents or dominance can be added (random effect $u_{K3}$) or not using markers with covariance identity (random effect $u_{I3}$) The covariance of $u_{K3}$ is proportional to the covariance of dominance effect describe above for the hybrids or to the Hadamard product of the VanRaden kinship of the hybrids. Model selection for the inclusion of the SCA component and the choice of its covariance structure is based on convergence of the model and AIC.

Figure 5:
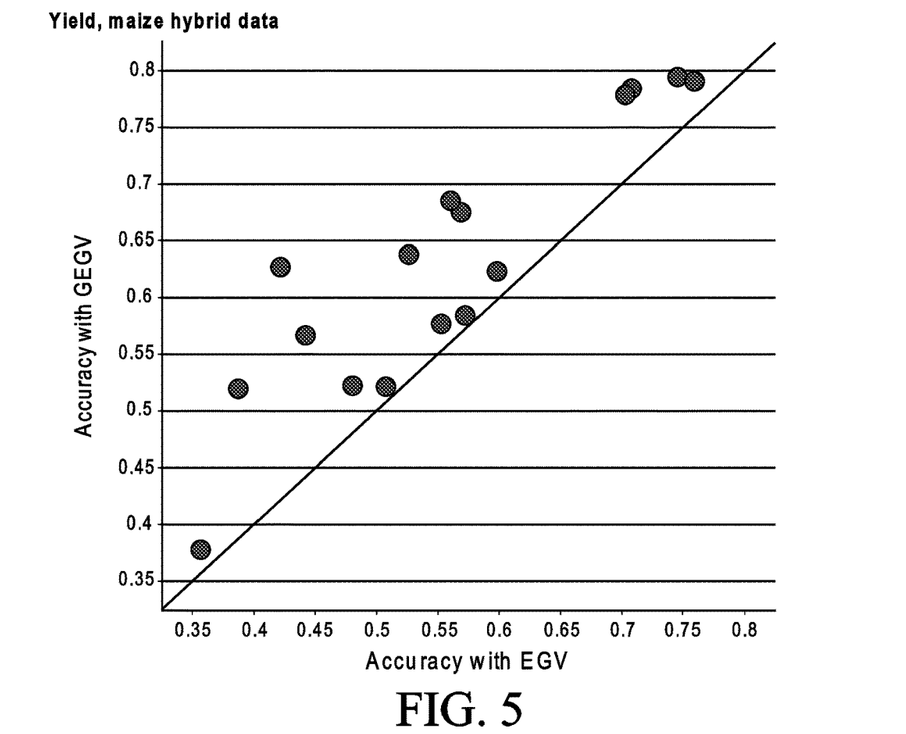
FIG. 5 shows, for hybrid maize yield, a comparison between the precision of the results obtained with the mixed model using molecular markers and, here, phenotype data (y axis) according to the invention, and the precision of the results obtained with a model using phenotype data only (x axis), FIG. 6 gives correlation values between estimated prediction and actual observation for both values obtained from the implementation of the mixed model according to an embodiment of the invention: agronomical and breeding values (respectively GEGV and GEBV)

FIG. 5 illustrates the gain with such a "pipeline" implementation on advanced trials of hybrid maize yield. The accuracy of predictions of hybrids phenotyped in year N using their yield data collected in year N−1 is plotted against the accuracy of predictions when adding markers to the analysis and including hybrids evaluated in supplementary years to N−1 (excluding year N). Each dot is a predicted year by dataset combination and the line represents y=x. If a dot is above the line, the mixed model with markers and phenotype (y axis) is more precise than the model with phenotype alone (x axis).

Figure 6:
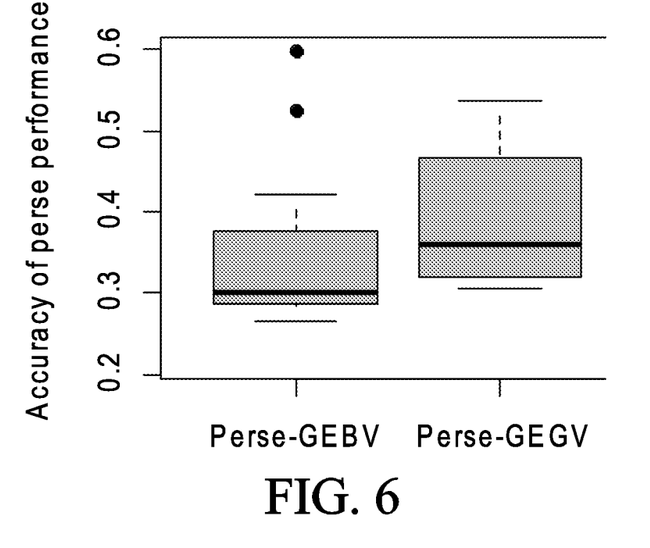

FIG. 6 shows the gain in accuracy for the prediction of unobserved maize hybrid when using a non-additive model instead of an additive model. The y axis values are related to a correlation between prediction and actual observation. The x axis is related to the GEBV (value as parent) and the GEGV (from which the true agronomical value GEAV is determined). The horizontal black line is the median in each case. It appears that the precision of the GEGV prediction (from which the agronomical value is then obtained) is better than the one based on parents (GEBV) in this case.

Figure 7:
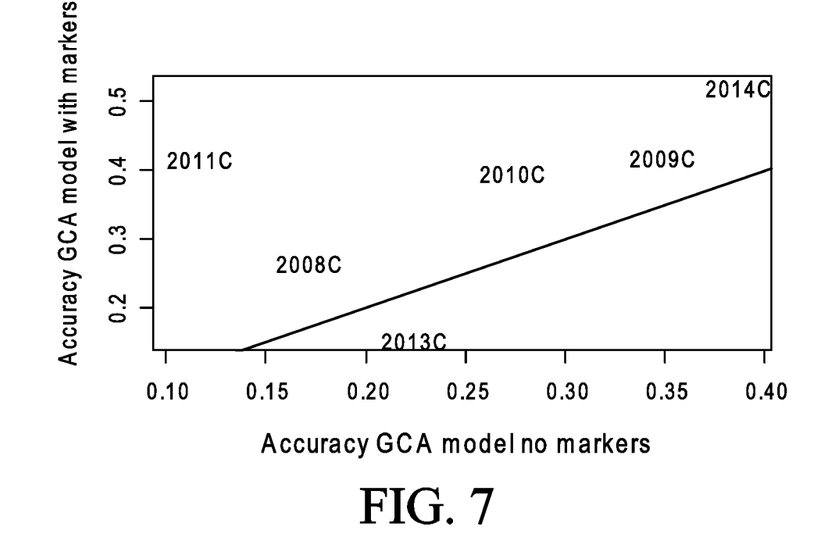
FIG. 7 shows the gain in accuracy, like in FIG. 5, for the prediction of hybrid rapeseed yield.

Like FIG. 5 above, FIG. 7 shows the gain in accuracy, but here for the prediction of hybrid rapeseed yield when adding marker to the phenotype data. If a dot is above the line, the model with markers is more precise than the model with phenotype alone.

Figure 8:
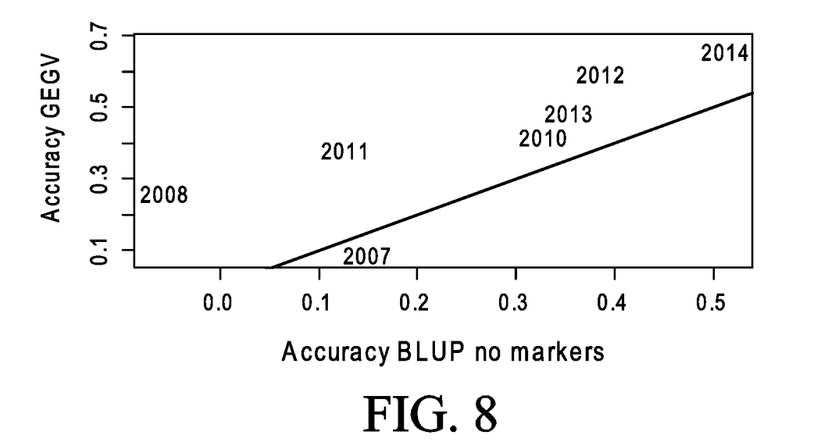
FIG. 8 shows the gain in accuracy, like in FIG. 5, for inbred performance with spring barley.

FIG. 8 shows a similar figure (with most of the points above y=x), but for inbred performance with spring barley.

Figure 9:
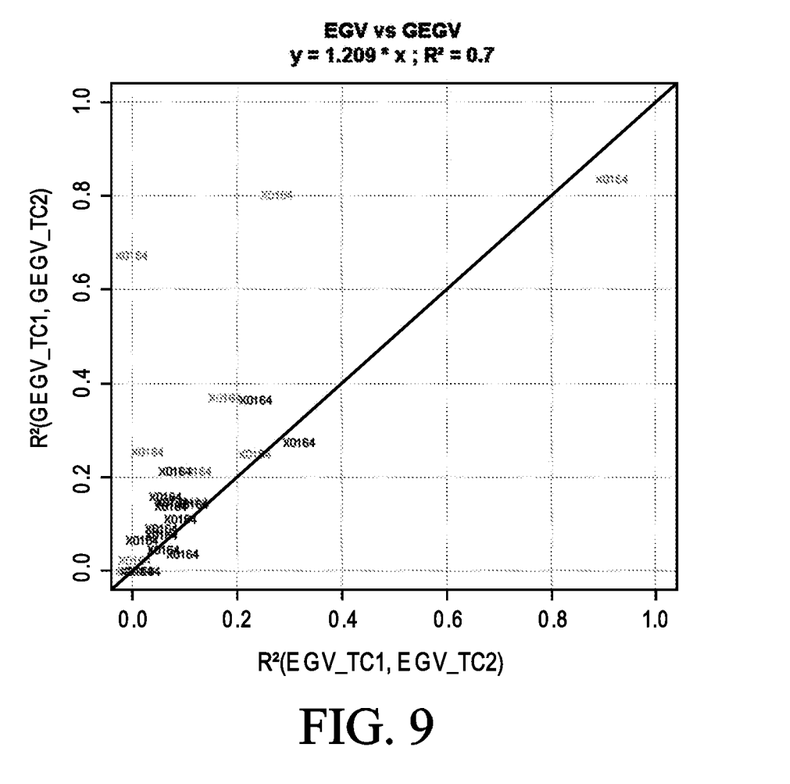
FIG. 9 shows the gain in accuracy, like in FIG. 5, for testcrosses with maize.

FIG. 9 shows a similar figure, but for testcrosses with maize (several datasets: first and second year of testcross trials). The average gain in precision is 20%.

Figure 10:
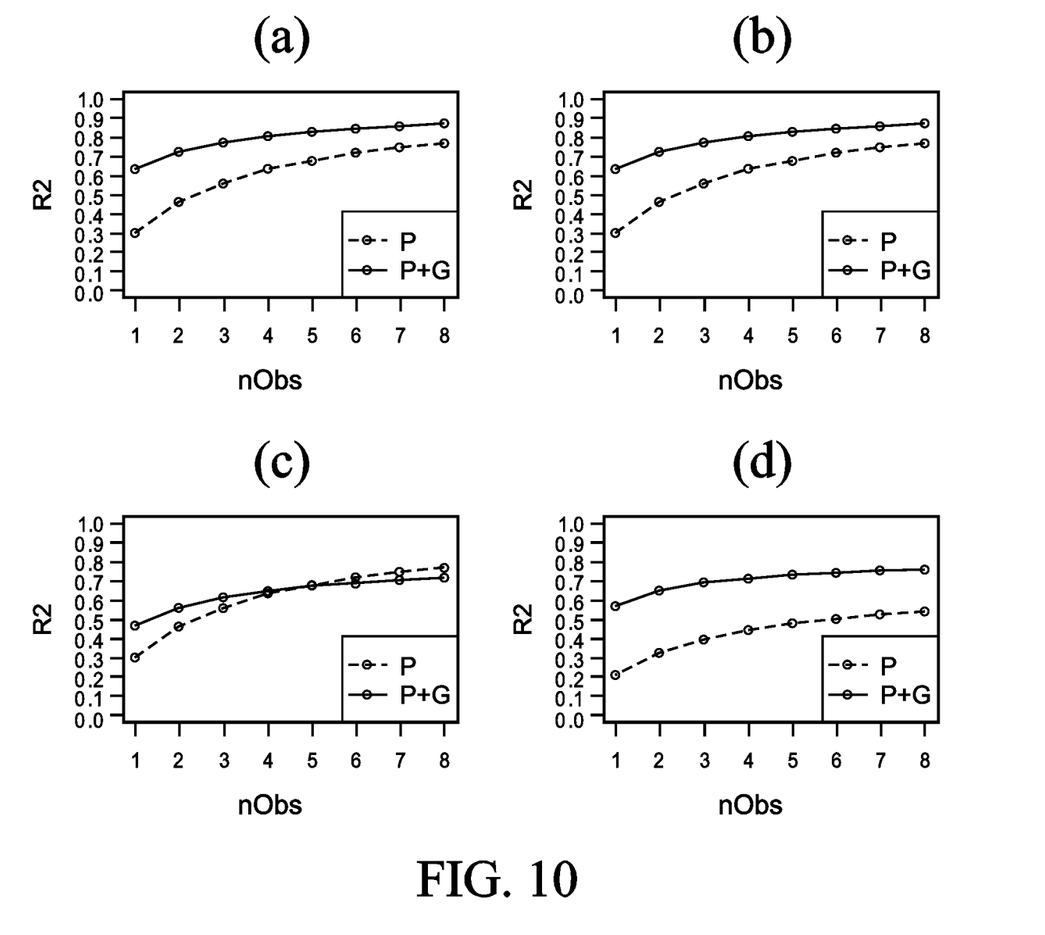
FIG. 10 shows the results of theoretical studies comparing the efficiency of selection on the agronomical value (FIGS. 10a and 10c) and on breeding value (10b and 10d) of phenotype data alone (dashed lines) and of phenotype plus markers data (solid lines), when epistasis is present (30% of variance) (FIGS. 10c and 10d) or not (FIGS. 10a and 10b) and the P+G model does not capture epistasis.

FIG. 10 shows the results of theoretical studies comparing the efficiency of selection on the agronomical value (FIGS. 10a and 10c) and on breeding value (10b and 10d) of phenotype data alone (dashed lines) and of phenotype plus markers data (solid lines) if a simple model (like GBLUP as used in step S49 of FIG. 4) is used. In the presence of epistasis (30% of variance) (FIGS. 10c and 10d), the precision of selection based on phenotype plus markers (P+G) can be inferior to the one based on phenotype alone (P) if epistasis is not modelled. This is not the case if epistasis is not present (FIGS. 10a and 10b).

Of course, the invention can be performed by a computer device or a computer system including one or several data entries (from one or several databases for example), and having a core architecture as shown in the very schematic and simplified FIG. 3.

The present invention can also be embedded in a computer program product, which comprises all the features enabling the implementation of the method described herein, and which, when loaded in an information processing device or system, causes the information processing device or system to perform the method of the invention. Computer program means or computer program in the present context means any expression, in any language, code or notation, of a set of instructions intended to cause a computer system or device having an information processing capability to perform a particular function either directly or after the conversion to another language. Such a computer program can be stored on a computer or machine readable medium allowing data, instructions, messages or message packets, and other machine readable information to be read from the medium. The computer or machine readable medium may include non-volatile memory, such as ROM, Flash memory, USB key, Disk drive memory, CD-ROM, and other permanent storage. Additionally, a computer or machine readable medium may include, for example, volatile storage such as RAM, buffers, cache memory, and network circuits. Furthermore, the computer or machine readable medium may comprise computer or machine readable information in a transitory state medium such as a network link and/or a network interface, including a wired network or a wireless network, that allow a device to read such computer or machine readable information.

The present invention is not limited to the description provided above as an example of embodiment; it encompasses possible variants.

An automatic selection of the best statistical model for measuring the genetic value (and breeding value, as well) has been described above with reference to FIG. 4. The model usually includes marker and phenotype information. However, in the model selection step, an alternative model which can be considered might not include markers, in an extreme case. Thus, the "best statistical model" can reject the use of molecular information, if needed.

The true agronomical value can be estimated furthermore for non phenotyped plants. For example, the model can also work to predict individuals with no observations on their own.

Furthermore, the Gaussian kernel in the method above can be used to estimate the covariance between individuals and capture non-additive effects, or another covariance estimator based on a direct product of the marker-based kinship can be used to capture pairwise epistatic interactions. However, other covariance estimator capturing non-additive effects can be used.

Advantageously, when the method of the invention is applied to hybrid crops performance prediction (with a male and female effect), a dominance effect can be fitted, and/or possibly also with an epistatic component based on markers fitted to capture heterosis, and/or possibly also with an effect capturing heterosis based on phenotype alone.

The model described above may include an additional fixed effect covariate to model the effect of major QTLs (QTL for "Quantitative Trait Loci") or genes on the trait. The model may give simultaneous analysis of several traits, with a covariance estimated between traits, and/or possibly with the same trait in different locations, years or groups of locations being treated as different traits. The covariance estimated between traits can then be used to analyze the trial network.

The model described above may include further a tester effect for testcross data (like shown on FIG. 9).

As described above, the method includes in the first steps an automatic quality control of molecular marker data (on data such as a percentage of missing data per individual and marker, on congruence with pedigree data, on expected heterozygosity rate). It may include further an automatic quality control of the phenotype data to remove data points with value out of an expected range, and possibly also an automatic quality control of the phenotype data to remove data points that might create numerical problems with the algorithm (e.g. locations with very few individuals). In a same or alternative embodiment, other tests to control data quality can be performed, such as an automatic fitting of a factor as fixed or random depending on the number of levels of that factor and elimination of data from the model if a quality score collected by experimenters is below a threshold. A cut-off step can be provided also to prevent from false results if the dataset is too small to be analyzed correctly. Moreover, the automatic detection and removal of outliers can be applied to outlier observations and/or to outlier individuals based on standardized residuals.

Finally, backsolving in the method according to the embodiment shown on FIG. 2 makes it possible to derive marker effects for the "additive" part. This method using markers effect makes it possible to quickly predict new unphenotyped individuals and thus to predict the variance of a cross using simulation or by analytical means.

The invention claimed is:

1. A computer implemented method for predicting an agronomical value and a breeding value of a plant belonging to a population, the method comprising:
    obtaining at least some genotypic data from a first subset of lines from the population;
    obtaining at least some phenotypic data from a second subset of lines from the population;
    providing a statistical model;
    inputting the genotypic data and the phenotypic data in the statistical model;
    using the statistical model to output an agronomical value estimated for the plant, and a predicted breeding value estimated for the plant as a parent, the statistical model being a mixed model combining fixed effects and random effects, the random effects including at least non-additive genetic effects; and
    predicting a crop performance based on the agronomical value.

2. The method according to claim 1, wherein the genotypic data comprise genetic markers data.

3. The method according to claim 1, wherein the mixed model further receives, as input, phenotypic data of the plant.

4. The method of claim 3, wherein the phenotypic data comprise field trial information data.

5. The method according to claim 1, wherein the mixed model comprises a Genomic Best Linear Unbiased Prediction (GBLUP).

6. The method according to claim 1, wherein marker-based kinships including at least a Gaussian Kernel are used to estimate a covariance between plant individuals and capture non-additive genetic effects.

7. The method according to claim 1, further comprising estimating at least one of a genetic dominance effect and a non-additive effect based on genotypic data to capture heterosis, so as to predict hybrid crop performance.

8. The method according to claim 1, wherein the statistical model further receives, as input, phenotypic data of the plant, and wherein the statistical model analyzes simultaneously a plurality of phenotype traits with at least one covariance estimated among:
    a covariance estimated between traits, and
    a covariance estimated for a same trait, between a plurality of different environments.

9. The method according to claim 1, wherein the mixed model uses at least one additional fixed effect covariate to model an effect of genotypic data on phenotypic data of the plant.

10. The method according to claim 1, wherein the mixed model has heterogeneous residuals.

11. The method according to claim 1, wherein the step of providing comprises selecting and then providing the statistical model, the model being selected among a plurality of candidates of statistical models, based on tests to fulfill a criterion of predictiveness.

12. The method according to claim 1, further comprising, before inputting the genotypic data and the phenotypic data in the statistical model, filtering at least the genotypic data so as to remove at least samples having incomplete data among the genotypic data and the phenotypic data.

13. The method according to claim 1, wherein, before inputting the genotypic data and the phenotypic data in the statistical model, outlier phenotypic observations are detected in the phenotypic data and removed from the phenotypic data before inputting the phenotypic data in the statistical model.

14. A device for predicting an agronomical value of a plant, comprising a circuit for performing the method of claim 1, the circuit including at least:
    an input configured to receive at least some genotypic data and some phenotypic data;
    a storage medium storing program instructions;
    a processor configured to cooperate with the storage medium to execute the method; and
    an output configured to deliver at least the agronomical value of the plant and a predicted breeding value estimated for the plant.

15. A non-transitory computer storage medium storing computer program instructions which, when executed by a computer, are configured to cause the computer to carry out a method for predicting an agronomical value and a breeding value of a plant belonging to a population, the method comprising:
    obtaining at least some genotypic data from a first subset of lines from the population;
    obtaining at least some phenotypic data from a second subset of lines from the population;
    providing a statistical model;
    inputting the genotypic data and the phenotypic data in the statistical model;
    using the statistical model to output an agronomical value estimated for the plant, and a predicted breeding value estimated for the plant as a parent, the statistical model being a mixed model combining fixed effects and random effects, the random effects including at least non-additive genetic effects; and predicting a crop performance based on the agronomical value.

\* \* \* \* \*